(12) United States Patent
Potthoff

(10) Patent No.: US 6,553,249 B1
(45) Date of Patent: Apr. 22, 2003

(54) DIAGNOSTIC METHOD AND DIAGNOSTIC MEANS USED IN DELIVERING A MEDICAMENT TO A PATIENT

(76) Inventor: Klaus Potthoff, Storgaten 17, S-352 31 Växjö (SE)

( * ) Notice: Subject to any disclaimer, the term of this patent is extended or adjusted under 35 U.S.C. 154(b) by 0 days.

(21) Appl. No.: 09/700,958

(22) PCT Filed: May 25, 1999

(86) PCT No.: PCT/SE99/00889

§ 371 (c)(1),
(2), (4) Date: Nov. 21, 2000

(87) PCT Pub. No.: WO99/61070

PCT Pub. Date: Dec. 2, 1999

(30) Foreign Application Priority Data

| | | |
|---|---|---|
| May 26, 1998 | (SE) | 9801837 |
| Oct. 28, 1998 | (SE) | 9803718 |

(51) Int. Cl.[7] ............................................. A61B 5/055
(52) U.S. Cl. ........................ 600/420; 604/48; 604/500; 604/514; 604/93.01; 604/285
(58) Field of Search ................................ 600/420, 431; 424/9.3; 604/48, 500, 514, 516, 93.01, 285, 287

(56) References Cited

U.S. PATENT DOCUMENTS

| | | | |
|---|---|---|---|
| 3,939,259 A | 2/1976 | Pescetti | 424/20 |
| 5,323,780 A | 6/1994 | Briggs et al. | 128/653.4 |
| 5,462,053 A | 10/1995 | Briggs et al. | 128/653.4 |

FOREIGN PATENT DOCUMENTS

| | | |
|---|---|---|
| DE | 19745890 C1 | 3/1999 |
| WO | 94/03210 | 2/1994 |
| WO | 95/02831 | 1/1995 |
| WO | 98/11922 | 3/1998 |

*Primary Examiner*—Ruth S. Smith
(74) *Attorney, Agent, or Firm*—Davis & Bujold, P.L.L.C.

(57) ABSTRACT

The present invention relates to a diagnostic method used to indicate the migration of a medicament through the digestive apparatus and resorption during this migration, with the use of a negative MRI-contrast agent and a positive contract substance, introduced into gelatin capsules. The gelatin capsules are arranged as inner capsules in a common outer capsule, which is provided with barium sulphate in such an amount, relative to the specific gravity of the contents of the stomach, so that the capsule will be able to sink through the contents of the stomach and reach the small intestine without a substantial time-delay. The invention also relates to a diagnostic apparatus to carry out the diagnostic method.

9 Claims, 1 Drawing Sheet ized with radioactive isotopes. This certainly facilitates the finding of the capsule, but it subjects the examined person to radiation, which should be avoided.

DIAGNOSTIC METHOD AND DIAGNOSTIC MEANS USED IN DELIVERING A MEDICAMENT TO A PATIENT

FIELD OF THE INVENTION

The present invention relates to a diagnostic method and a diagnostic means used in carrying out the method.

In certain circumstances it is desirable but difficult to prove the existence of a medicament in its surroundings in and on its way through the digestive apparatus.

Conventional methods use capsules, which are labeled with radioactive isotopes. This certainly facilitates the finding of the capsule, but it subjects the examined person to radiation, which should be avoided.

Another method tested, by means of magnetic resonance imaging (MRI), shows the existence of a tablet shown by a negative contrast agent (iron oxide+ barium) in the digestive apparatus, this tablet being shown as a black silhouette against a white background of the conventional liquid positive MRI-contrast agent Magnevist enteral.

This method has a drawback, since even if it is easy to visualize this black tablet in the ventricle (stomach) in a white sea of liquid contrast agent, this very contrast agent, when being transferred to the small intestine, apparently is mixed with other digestive liquids, which results in an uneven, streaked filling of the small intestine, the tablet also being dissolved too quickly. Thus, an indication of the existence of the tablet is not possible. Various efforts to make the positive contrast agent more paste-like have not yielded any satisfactory results. Examinations with Magnevist enteral and a negative contrast agent, i.e. an agent which is black in an MRI-display, require, that the stomach is purged before the examinations.

U.S. Pat. No. 3,939,259 teach how to fill a capsule with tablets and delay the release of medicaments by a layer of beeswax.

Barium sulphate and iron oxide in a water solution are used as negative contrast agents according to U.S. Pat. No. 5,323,760.

WO 94/03210 relates to oils, used as positive contrast agents.

Various useful and also advantageous details are individually known through these publications, but they are not combined in a particular way to speed up a diagnosis and make it more reliable, and so clear and simple that certain preparatory measures, such as purging, completely or partially can be dispensed with. Also no efforts apparently have been spent to develop a simple, variable construction, which is easy to adapt to various diagnostic requirements and desires. Also, it has not been found, that so far there has been a generally expressed desire to design a capsule having tracer functions and which can be charged with an optional module, which contains a substance to be examined.

The object of the present invention is to counteract and as far-reachingly as possible overcome the above-mentioned drawbacks. Additional objects comprise the development of the state of the art in this field in various respects.

These objects are achieved in accordance with the invention by designing a diagnostic method of the type described in the specification.

A negative MRI-contrast agent Abdoscan is on the market. This agent is mixed with water to a water solution, which, when it has been swallowed, becomes pudding-like in consistency in the digestive apparatus and fills e.g. the small intestine relatively uniformly, which substantially facilitates the finding of the white signal capsule in this uniform black sea of contrast agent. This is an obvious advantage compared to said liquid positive, i.e. white, contrast agents.

The following problem appeared; to develop a capsule, which through a positive contrast agent filling is clearly visible in a negative contrast agent and which only in the lower part of the digestive apparatus releases the substance to be examined and also is not toxic. This substance, i.e. the cargo portion, is allowed to be dissolved depending on its composition, which varies from substance to substance, in interaction with the biochemical environments in the body in various places along the movement path.

It has been found that certain deep-sea fish oil capsules on the market yield an excellent positive contrast in MRI, i.e. gives a white picture. Other natural or synthetic organic non-toxic substances may also be used.

However, such capsules are dissolved too quickly, i.e. already in the stomach and also, they have the negative property in the stomach of being lighter than water. Thus, they float on top of the contents of the stomach and do not reach the lower outlet of the stomach.

Consequently, two such capsules are wrapped in a mixture of iron oxide+ barium sulphate powder in an empty gelatin capsule and two deep-sea fish oil capsules are chosen, since the signal picture which only one capsule gives, may look like the body's own structures, e.g. fat. In case the MRl-picture shows the two Inner capsules In front of each other, only a bright white point is visible. In order to decide, whether this is the capsule, the next picture is taken with a 90° angle in relation to the previous one and then, In the same plane, two bright white points, having the same size, are visible, obviously a picture of the capsule and not one of the body's own structures. In principle or alternatively, if is possible to choose such an oblong and/or a rectangular and/or an oval, inner capsule shape that, when said pictures are taken from different angles always at least one picture is obtained, which clearly differs from more common own structures of the body. As far as possible, in order to avoid taking pictures from different angles with great reliability and speed are able to identify the position of the capsule, it is also possible to give the capsule an asymmetrical shape as regards its contents in such a way, that one capsule side or end always tends to sink first, because this side or end contains substances having a larger weight and density, respectively. Alternatively, a small air inclusion can serve the same purpose. An iron oxide is chosen due to the fact that this compound, because of its negative (black) MRI-picture, yields an increased contrast around the positive (white) picture, which substantially facilitates the determination of its position. Barium sulphate is added because this compound substantially facilitates the displacement of the capsule through the force of gravity through the stomach and into the small intestine during the time when the patient, between the picture takings, is up and moves about. Tests without barium sulphate have shown that the capsule then is too light-weight, flows on top of the contents in the stomach and does not reach the small intestine within several house. Also, barium sulphate has a negative contrast effect, i.e. it gives a black picture in MRI.

Alternatively it is possible to put the signal substance in e.g. a gelatin capsule, which is wrapped up in a shell, which consists of a mixture of solid paraffin and barium sulphate.

It was found, that this functioned properly. An excellent contrast is seen between the two white oil capsules and the mixture of iron oxide and barium sulphate with its negative (black) MRI-picture and between the positive substance and the signal-negative shell respectively, which latter consists of paraffin plus barium sulphate.

In the human body there are no structures, which yield such a similar signal pattern in MRI, which substantially facilitates the finding of the capsule.

Also, the capsule is now so heavy, that it finds its way by itself to the lower outlet of the stomach.

With regards to the dissolution which is too quick, beeswax does not melt or is not dissolved at body temperatures. Thus, the dry gelatin capsule is provided on its outer side with liquid beeswax and has let the beeswax cool. The capsule is still sufficiently heavy to sink, thanks to the included barium. However, thanks to the beeswax, it has not even been dissolved when it reaches the anal opening, which is perfect from the point of view that it then also is not able to influence the examination of the substance, which is to be examined. Instead of beeswax, it is possible to use a layer, which consists of a mixture of solid paraffin (paraffinum solidum) and barium sulphate in order to obtain a protection of the capsule and, at the same time, the barium sulphate contributes to the necessary weight.

The substance to be examined is wrapped up in or is mixed with solid paraffin (paraffinum solidum). This solid paraffin portion constitutes the cargo portion itself, i.e. that portion, which is optional and can be united with the trace portion of the capsule. The release/dissolution takes place slowly or at a certain pH-value. It is done by coating the substance to be examined with a pH-sensitive substance. This method has been tested during several decades by the pharmaceutical industry and is used by routine in certain pharmacological preparations. Thus, the method allows a utilization of all this experience, how medicaments are to be mixed with paraffin in order to be released slowly and consequently in a careful way, or put in another way, intentionally during a longer time in order to provide the same medicament concentration during a long time.

Instead of beeswax another non-toxic substance can be used, which melts or dissolves only at higher temperatures than the temperatures of the body, e.g. at 40–50° C., and which at least during a sufficiently long time is able to resist the liquids in the body without dissolving in the wrong intestinal section and with that effect respectively, that it is dissolved in the proper intestinal section and also during a long time.

Tests have shown, that it is possible to indicate the capsule all the way from the stomach and through the entire small intestine and also in the colon in its section close to the anal opening.

The present invention is not limited to what has been stated above, which only is to be considered a non-limiting embodiment, which can be modified and supplemented in an arbitrary fashion within the scope of the inventive idea and the following claims respectively.

Instead of paraffin other substances can be used, e.g. waxes plus non-toxic substances heavier than water instead of barium sulphate.

The substance to be examined can either be included in the outer capsule/the outer shell in the form of a separate capsule (the cargo capsule) or be mixed with the chemically inert substance of the shell.

It is found that a capsule, according to the invention, gives a clear signal picture against the used contrast agent, that despite small amounts of substances remaining in the stomach and the intestines, the otherwise mandatory purging before the examination is not required. This results not only in a substantial relief for the patient, who avoids the inconvenience of having at least one day lost due to the purging, but also in another advantage. A purging leads to an increased mobility in the intestines. This increase mobility is a substantial drawback during MRI-examinations, since the picture taking per se takes time (reminding one of the old-fashioned photographing, when it was necessary to stand absolutely still for a long period of time in order to obtain a shape picture). However, it is not possible to stop the movement of the intestines by sheer willpower. On the other hand, the intestines hold substantially steady, if no purging is used and one keeps fasting from the evening before the examination and then in the morning swallows the contrast agent and the capsule, which provides excellent, sharp pictures despite certain small remaining amounts of substances in the stomach/intestines.

None of the other described diagnostic means has had any substantial medical impact. None of them is said to be used commercially despite the fact, that these means have been known for several decades.

The invention will now be described, by way of example, with reference to the accompanying drawings in which.

Figure 1:
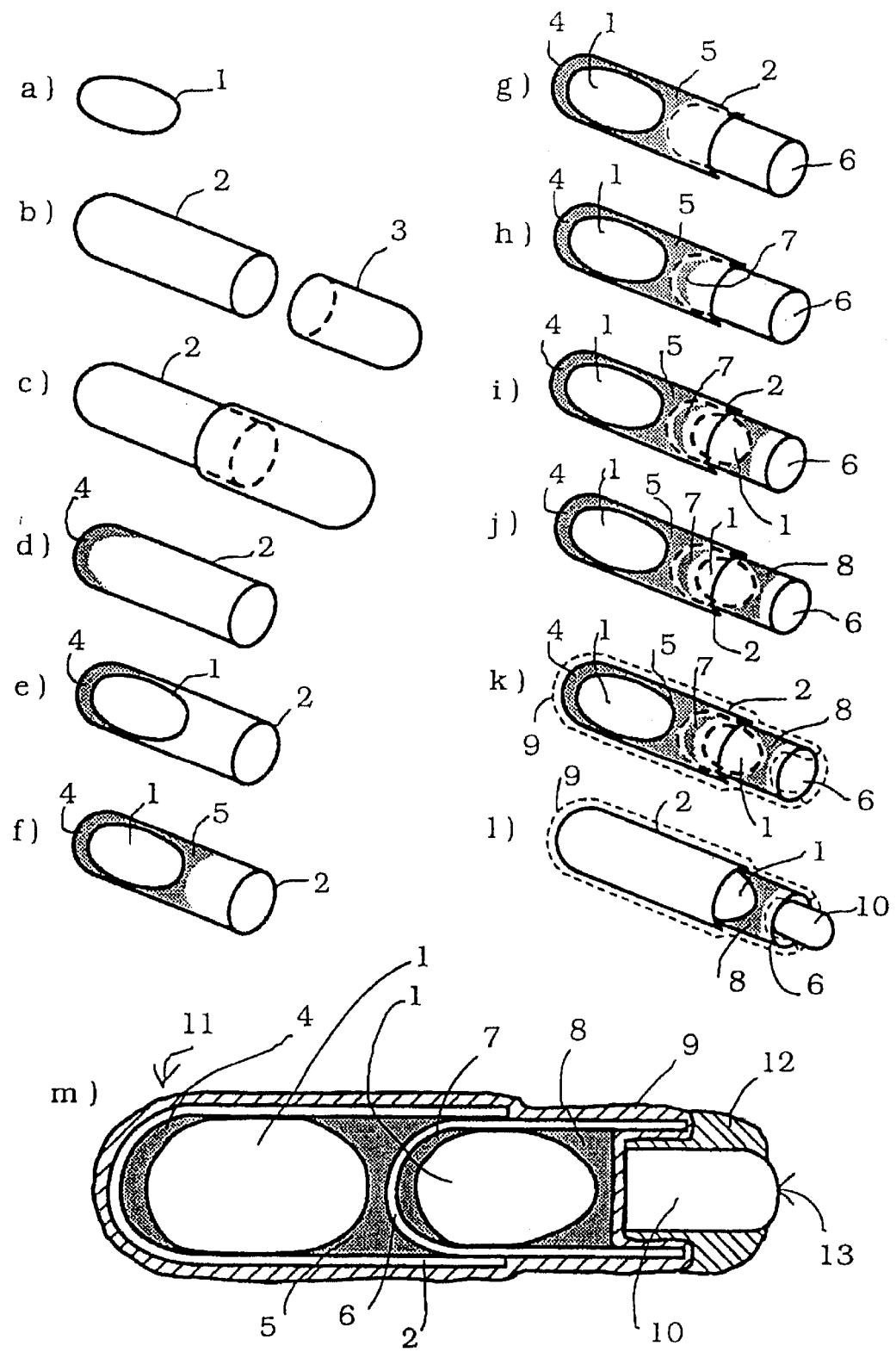
FIG. 1a is an inner capsule 1, which contains a positive contrast substance.
FIG. 1b is a lower portion 2 and upper portion 3 of a conventional outer capsule; in this example, only the lower portion is used as a n outer capsule.
FIG. 1c is an otherwise possible outer capsule, which consists of a lower portion plus an upper portion.
FIG. 1d is an application of a first dose 4 of a heavy substance on the bottom of the lower portion, e.g. barium sulphate, possibly barium sulphate and iron oxide.
FIG. 1e is an inner capsule, inserted in the lower portion, prepared in this way, avoiding air inclusions. Alternatively, it is in this case possible to form a possibly desirable small air inclusion in order to facilitate a vertical positioning of the means in e.g. the stomach.
FIG. 1f is a second dose 5 of a heavy substance, applied on top of the inserted inner capsule.
FIG. 1g is a lower portion 6 of a second outer capsule, inserted with forced fit into the first lower portion, air inclusions being avoided.
FIG. 1h is a third dose 7 of a heavy substance, inserted into the second lower portion.
FIG. 1i is a second inner capsule, inserted into the second lower portion, prepared in this way.
FIG. 1j is a fourth dose 8 of a heavy substance, inserted into the second lower portion on top of the second inner capsule.
FIG. 1k is a thin layer 9 of liquid beeswax, applied to the outside of the construction, obtained in this way, and also to the inside from the outside available portion of the second lower portion and to the free outside of said fourth dose 8.

FIG. 1l is a cargo portion 10, which consists of or contains a substance, which is to be examined, which substance in a typical case is a drug substance, mixed with paraffin and is inserted into the open end of the second lower portion to fill this and be joined with its outer paraffin portions with the wax, which is still liquid; and FIG. 1m is the border area between the wax layer and said paraffin portions, fused together in a way similar to how thermoplastic materials fuse together. In this way some form of alloy or soldering together or adjacent portions is obtained and is guaranteed in a far-reaching way, that this entire construction is kept together up to the end, i.e. until this means has left the body. In order to facilitate the swallowing of said means a part of the cargo portion, particularly the sides, which are parallel to the lower portions, can be provided with a paraffin layer 12, a soft transition zone between wax layer 9 and cargo portion 10 being obtained. However, the rest of the outer side of the latter, particularly its outer free end 13, is not covered by the paraffin layer, a dissolution, a leaching or the like in relation to present liquids in the body being possible.

The present invention is not limited to the embodiments described above and/or shown in the accompanying drawings but can be modified and supplemented in an arbitrary fashion within the scope of the inventive idea and the following claims. Thus, barium sulphate and/or iron oxide are only to be regarded as examples. They can of course be replaced with other suitable substances, provided such substances are sufficiently heavy and satisfactorily function as contrasting agents respectively. Also, the term capsule and capsules respectively can be replaced with other forms of enclosing/limiting means, e.g. various forms of coating and/or treatment and filling respectively during a preferably fully automatic production process. By using a powdery substance or substance mixture the inner capsules will not be exposed to moisture. However, in case the material of the inner and outer capsules respectively is resistant to e.g. a water solution, which contains said heavy substance and contrast agent respectively, it is of course possible to use such a solution instead to a powder.

What is claimed is:

1. A method of delivering a medicament to a digestive tract of a patient to facilitate a magnetic resonance imaging diagnosis of the patient's digestive tract, the method comprising the steps of;

filling at least one inner gelatin capsule with a first MRI contrast agent;

inserting the at least one inner gelatin capsule into an outer capsule;

including the medicament with the outer capsule or in a material forming the outer capsule for release in the digestive tract;

introducing the outer capsule and the at least one inner capsule into a patient's stomach;

passing the outer capsule containing the at least one inner capsule through the parent's stomach to a small intestine of the patient faster than other contents of the patient's stomach; and employing barium sulphate in the outer capsule as a second MRI contrast agent to facilitate the passing of the at least one inner capsule through the patient's stomach to the small intestine faster than the other contents of the stomach.

2. The method of delivering a medicament to a patent's digestive tract according to claim 1, further comprising the steps of;

inserting iron oxide into the outer capsule as an additional MRI contrast agent to facilitate distinguishing the at least one inner gelatin capsule containing the first MRI contrast agent;

providing a natural or synthetic organic non-toxic substance as the first MRI contrast agent;

controlling the dissolution of the outer capsule and the release of the medicament by coating the outer capsule with at least one of beeswax or a non-toxic substance having a melting temperature higher than a body temperature and which does not dissolve in contact with gastric stomach fluids of the patient's stomach.

3. The method of delivering a medicament to a digestive tract of a patient according to claim 2, further comprising the step of forming the outer capsule from a mixture of solid paraffin and beeswax.

4. The method of delivering a medicament to a digestive tract of a patient according to claim 3, further comprising the steps of mixing the medicament with a chemically inert substance and inserting the mixture into a cargo capsule attached to the outer capsule.

5. The method of delivering a medicament to a digestive tract of a patient according to claim 4, further comprising the step of inserting at least two inner gelatin capsules into the outer capsule wherein so that when the at least two inner capsules are observed from a desired angle the at least two inner capsules yield a noncircular or non-single point-shaped contrasting picture.

6. The method of delivering a medicament to a digestive tract of a patient according to claim 2, further comprising the step of employing deep sea fish oil as the natural or synthetic organic non-toxic substance.

7. The method of delivering a medicament to a digestive tract of a user according to claim 1, further comprising the step of;

introducing iron oxide into the outer capsule to enhance the visual distinction between the first MRI contrast agent and the iron oxide in the outer capsule to improve detection in an MRI picture.

8. The method of delivering a medicament to a digestive tract of a patient according to claim 1, further comprising the step of at least one of the outer capsule and the inner capsule containing a mixture of solid paraffin and barium sulphate.

9. The method of delivering a medicament to a digestive tract of a patient according to claim 1, further comprising the step of binding at least one of the first, second and additional MRI contrast agents by one of wax and paraffin, and forming at least one of the outer capsule and the at least one inner gelatin capsule from one of the wax and paraffin binding the at least one of the first, second and additional MRI contrast agents.

\* \* \* \* \*